(12) United States Patent
Gentillin et al.

(10) Patent No.: US 6,600,812 B1
(45) Date of Patent: Jul. 29, 2003

(54) METHOD AND APPARATUS FOR PROVIDING EMERGENCY RESPONSE INFORMATION

(75) Inventors: John C. Gentillin, Franklin Park, NJ (US); Alan North, Berkeley, CA (US)

(73) Assignee: Smart911, Inc., Berkely, CA (US)

( * ) Notice: Subject to any disclaimer, the term of this patent is extended or adjusted under 35 U.S.C. 154(b) by 0 days.

(21) Appl. No.: 09/563,174

(22) Filed: May 2, 2000

Related U.S. Application Data

(60) Provisional application No. 60/187,425, filed on Mar. 7, 2000.

(51) Int. Cl.$^7$ .............................................. H04M 11/00
(52) U.S. Cl. ...................................................... 379/45
(58) Field of Search ............................ 379/45, 37, 38, 379/39, 40, 265.09; 370/352

(56) References Cited

U.S. PATENT DOCUMENTS

| | | |
|---|---|---|
| 5,195,126 A | 3/1993 | Carrier et al. |
| 5,228,449 A | 7/1993 | Christ et al. |
| 5,311,569 A | 5/1994 | Brozovich et al. |
| 5,334,974 A | 8/1994 | Simms et al. |
| 5,347,568 A * | 9/1994 | Moody et al. ................. 379/45 |
| 5,398,277 A * | 3/1995 | Martin, Jr. et al. ........... 379/39 |
| 5,444,760 A | 8/1995 | Russ |
| 5,761,278 A | 6/1998 | Pickett et al. |
| 5,787,429 A * | 7/1998 | Nikolin, Jr. .................. 379/37 |
| 5,805,670 A | 9/1998 | Pons et al. |
| 5,815,417 A | 9/1998 | Orr et al. |
| 5,890,129 A | 3/1999 | Spurgeon |
| 5,935,060 A | 8/1999 | Iliff |
| 5,967,975 A | 10/1999 | Ridgeway |
| 5,971,931 A | 10/1999 | Raff |
| 6,028,537 A | 2/2000 | Suman et al. |
| 6,064,722 A * | 5/2000 | Clise et al. ................... 379/37 |

FOREIGN PATENT DOCUMENTS

| | | |
|---|---|---|
| WO | WO 99/56144 | 11/1999 |
| WO | WO 00/40038 | 7/2000 |

* cited by examiner

Primary Examiner—Stella Woo

(57) ABSTRACT

A computer architecture and data handling paradigm useful in providing data records from subscribers in time critical response situations.

22 Claims, 5 Drawing Sheets

METHOD AND APPARATUS FOR PROVIDING EMERGENCY RESPONSE INFORMATION

CROSS REFERENCE TO RELATED APPLICATIONS

This application claims priority from provisional patent application No. 60/187,425 filed Mar. 7, 2000.

FIELD OF THE INVENTION

The present invention relates to the field of providing data and services during an emergency response. More particularly, the present invention, in various specific embodiments, involves methods, systems, apparatus, and/or data formats directed to providing reliable and extensible emergency response data services using an open source architecture.

BACKGROUND OF THE INVENTION

Recently, there has been considerable interest in providing additional enhanced data to various individuals that may be involved in a response to a request for emergency assistance. Such services generally are sometimes referred to as enhanced 911 services (e911). A number of United States patents have been issued discussing various aspects regarding enhanced 911 services. These patents include:

U.S. Pat. No. 5,805,670 Private Notification System For Communicating 9-1-1-Information (Pons);

U.S. Pat. No. 5,761,278 Integrated Data Collection And Transmission For 9-1-1-Calls For Service (Pickett);

U.S. Pat. No. 5,334,974 Personal Security System (Simms);

U.S. Pat. No. 5,890,129 System for Exchanging Health Care Insurance Information (Spurgeon);

U.S. Pat. No. 5,815,417 Method For Acquiring And Presenting Data Relevant To An Emergency Incident (Orr);

U.S. Pat. No. 5,444,760 Routing of Special Emergency Calls (Russ);

U.S. Pat. No. 5,935,060 Computerized Medical Diagnostic and Treatment Advice System Including List Base Processing (Iliff);

U.S. Pat. No. 5,195,126 Emergency Alert And Security Apparatus And Method (Carrier);

U.S. Pat. No. 5,311,569 Line-Based Public Safety Answering Point (Brozovich).

Pons discusses a private notification system for notifying others when an emergency call is occurring. An example given is notifying parents who may be away from home when a 911 call is made from their home. In relation to one embodiment, an emergency care information database is discussed as providing emergency care information supplied by a subscriber to a user. The emergency care information database is briefly described as accessible by a control center (the CCC) through the emergency care database access point and includes a medical history, insurance, police, and fire emergency information provided by the subscriber.

Simms discusses a personal security system wherein a mobile unit communicates emergency data to a central dispatch unit. The mobile security unity communicates position information as well as personal information to a central dispatch operator.

Spurgeon discusses a system for exchanging health care insurance information between a variety of computerized databases using an information-exchange computer and data translations into an exchange database. A discussed system integrates computers that use mutually incompatible databases with an information-exchange system that can be visualized as a hub-and-spoke system, with the information exchange computer forming the hub. A discussed advantage is the increased speed with which claims are processed and paid and with which a subscriber may learn if a requested treatment will be paid for by the insurer. The system is described as a high-speed, computerized system as a continuous conduit for all aspects of payment authorization requests.

Russ discusses detecting a 911 call and retrieving additional data from a database and forwarding that data to a PSAP.

Orr discusses providing a variety of emergency response relevant data over the course of an emergency to a command center, including real-time information. Discussed data sources include land based, air-based, or space-based detection units, such as satellites or helicopters.

Pickett discusses an integrated data delivery service for 911 calls that uses a caller-id to automatically interrogates one or more databases to provide additional information to a responder. The discussed method integrates data as it is returned by one or more automatically interrogated databases and then transmits the data file a leased or dial up telephone line to a radio common carrier for broadcast to an end user. According to the description results from the various databases are merged before being transmitted to the responder. As shown in FIG. 2 of Pickett, all of the databases reside in a single computer or computer system 150.

These patents are incorporated by reference for the purposes of understanding background concepts related to the art.

While many different functions, features and techniques have been proposed associated with providing fast response data service, these features by and large have been directed to a single definitive source data system that must be continually updated with current data relevant to a fast response service. What these systems have failed to address, for the most part, is the fact that there is a tradeoff to be made between a tightly controlled, highly verified central data system and having access during an emergency response to the most relevant and most up-to-date data which may be in fact resident in a number of data sources.

For example, emergency medical personnel responding to an employee having a medical emergency in an office building, generally will want fast access to current medical and contact information regarding that employee. The most definitive and up to date version of that information is likely to be that resident in an employer human resources database. Data at a central data source, even if updated periodically, can have non-current data when accessed during the emergency response. Also, in many instances, it may be impractical to continually update data from a number of employee databases to a central data source.

As a further example, in some instances, data relevant to an emergency response may not be available prior to occurrence of the incident. For example, an insurance company may be set up to receive information about an emergency, such as a fire, occurring at the home of a policyholder. The insurance company may assign a representative to the incident as the incident is occurring based on the region in which the incident is located, the time of day, or various representative work loads. This assignment of an insurance company authorized representative may be highly relevant to resolving the incident, but the data is not available from the insurance company until the incident occurs. Thus, emergency response data systems that rely on preloaded databases cannot accommodate this type of changing data.

As a further example, in some instances, data relevant to an emergency response may be of such quality or quantity that it is not practical or desirable to collect and store it at a central location. An industrial site, for example, may wish to provide plant layout or industrial process information or information from real-time sensors or cameras. Furthermore, different installations may have very different format or configured data. Some locations may have just very basic data and other locations may have cameras or VRML formatted data. Emergency response data systems that rely on preloaded databases cannot easily accommodate this type of data.

What is needed is a method and/or apparatus for providing enhanced emergency response data reliably and in a decentralized manner.

SUMMARY

The present invention in various aspects may be embodied as a method or a system or an apparatus for providing an improved extended 911 or similar fast response data services. The invention provides an open data protocol method for making data from a variety of sources available during an emergency response. In a further aspect, the invention provides a method for collecting data from a variety of sources into a log for an emergency response, to assist a concerned individual in learning what is happening during an emergency response or to assist in follow-up to the emergency response.

The invention and various specific aspects and embodiments will be better understood with reference to the following drawings and detailed descriptions. In some of the drawings and detailed descriptions below, the present invention is described in terms of the important independent embodiment of an emergency response system. This should not be taken to limit the invention, which, using the teachings provided herein, can be applied to other situations. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims.

Furthermore, it is well known in the art that logic or digital systems and methods can include a wide variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification.

The functional aspects of the invention, as will be understood from the teachings herein, may be implemented or accomplished using any appropriate implementation environment or programming language, such as C++, Cobol, Pascal, Java, Java-script, HTML, dHTML, XML, etc.

All publications, patents, and patent applications cited herein are hereby incorporated by reference in their entirety for all purposes.

DESCRIPTION OF SPECIFIC EMBODIMENTS

In order to facilitate description, the following discussion will describe the present invention in terms of providing emergency response data, such as 911 emergency responses, during occurrence of an emergency. It will be understood to those of skill in the art, however, that aspects of the present invention also may be used during provision of other time-critical data. The invention should therefore not be taken as limited except as provided in the attached claims.

Figure 1:
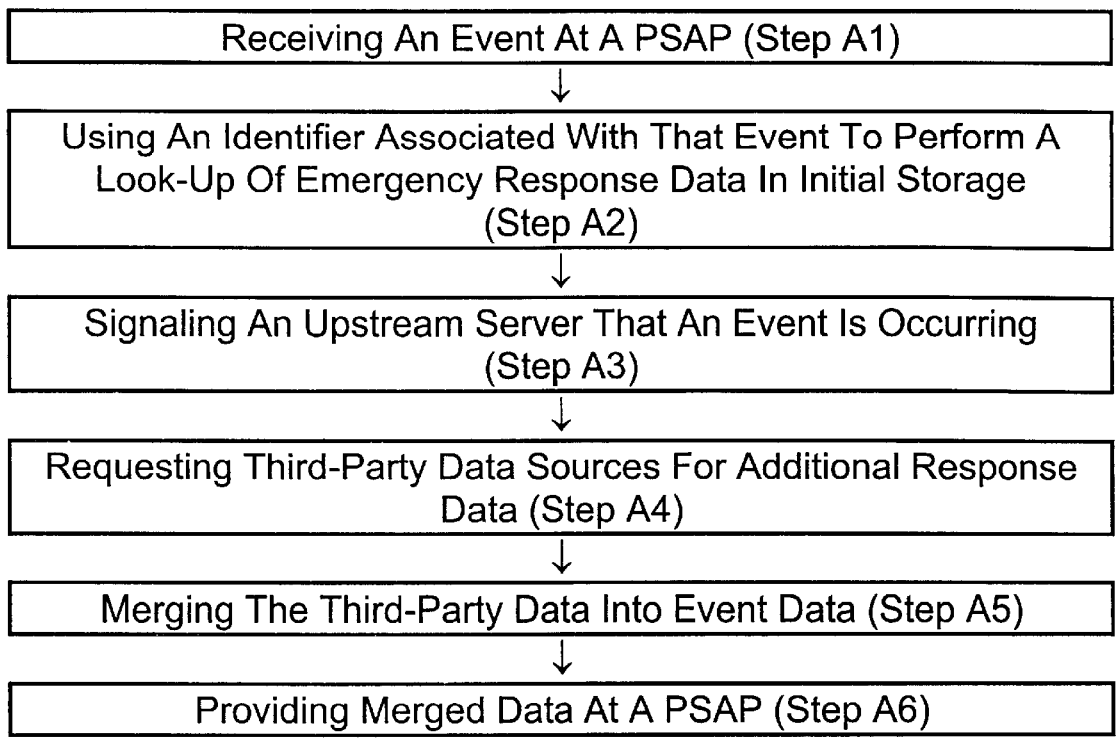
FIG. 1 is a flow chart showing a general method according to the invention.

In general terms, the present invention is directed to a method of providing emergency response data services. An illustration of the general method is-shown in FIG. 1, including the steps of: receiving an event at a PSAP (or other time-critical operator terminal or workstation) (Step A1); using an identifier associated with that event to perform a look-up of emergency response data in an initial (such as local) storage (Step A2); signaling an upstream server that an event is occurring (Step A3); requesting third-party data sources for additional response data (Step A4); when third-party data is received, merging the third-party data into event data (Step A5); and providing merged data at a PSAP (Step A6).

Figure 2:
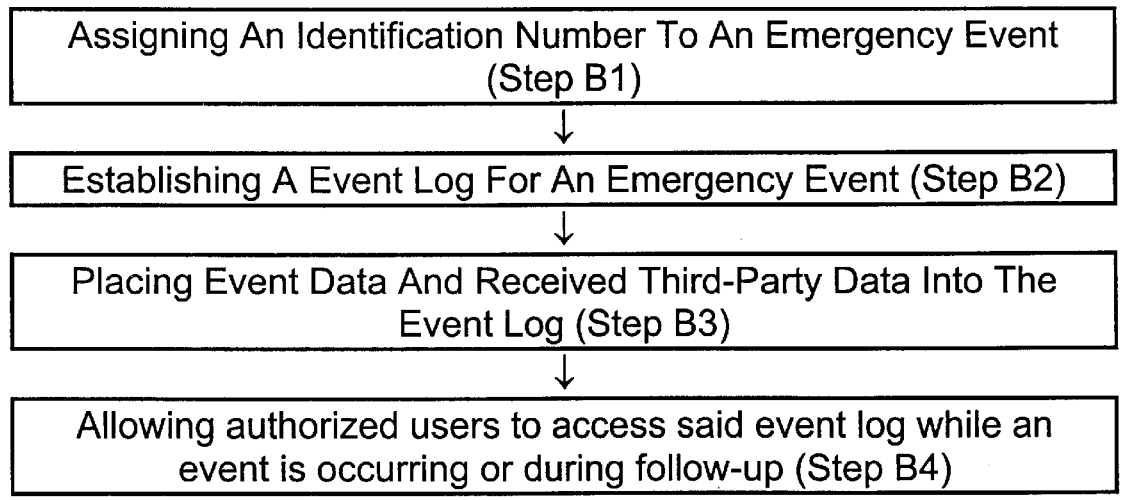
FIG. 2 is a flow chart showing a general method according to the invention.

In specific embodiments, the invention provides additional features and services related to emergency events, as illustrated in FIG. 2, including the steps of: assigning an identification number to an emergency event (Step B1); establishing an event log for an emergency event (Step B2); placing event data and received third-party data into the event log (Step B3); and allowing authorized users to access said event log while an event is occurring or during follow-up (Step B4).

Example System Architecture

Figure 3:
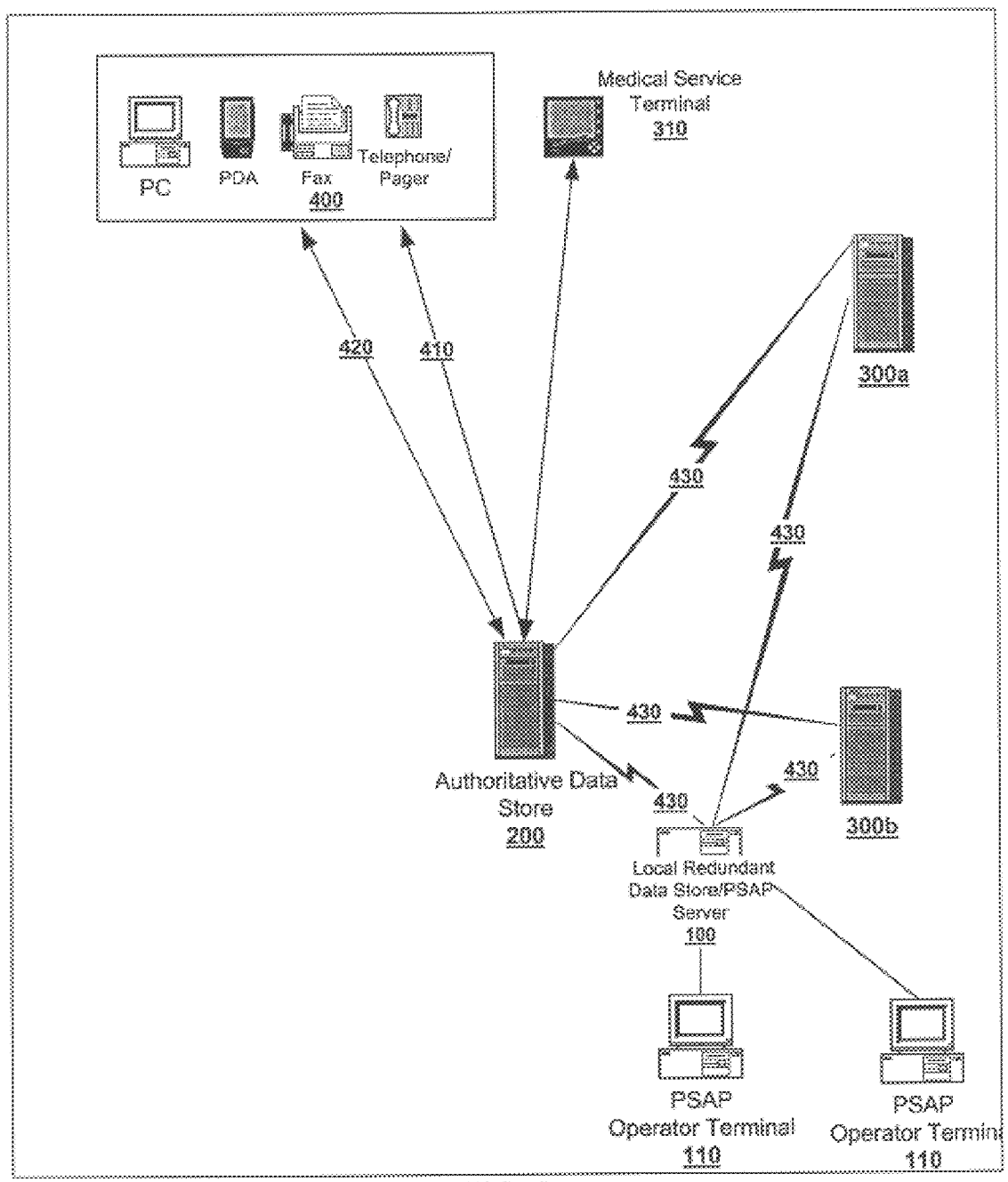
FIG. 3 is a block diagram showing an example system architecture data flow according to specific embodiments of the invention.

In a particular embodiment, the present invention can be understood as a system for exchanging extended 911 information among subscribers, third party information providers, and PSAPs. An example architecture for doing this is shown in FIG. 3.

In this example architecture, a local data store system 100 provides immediate response data to one or more PSAP terminals 110. In particular embodiments, system 100 is used to locally store data assigned to its associated PSAPs and to provide front line redundancy in the case that a connection to an upstream data store 200 is not available.

In specific embodiments, system 100 further forwards event data to upstream data hub 200, which handles additional data services as described below. The separation of the local data store 100 from the extended data services 200 is one important aspect of specific embodiments of the invention. While systems 100 and 200 could in fact be resident in a single physical computer system, their design and operation is such that the extended services provided by 200 do not delay the provision of data by 100.

In specific embodiments, an Authoritative Server may contain an authoritative version of stored subscriber data. Authoritative Servers may be location independent and many Authoritative Servers can hold the same subscriber information.

In specific implementations, at a PSAP, there may also be a Local Redundant Data Store (LRDS), such as 100. Each LRDS will be configured to hold a local copy of the subscriber information that is assigned to the PSAP. In specific embodiments, the LRDS will also hold a copy of query responses that were initiated from the PSAP terminal, even if that data is not generally assigned to that local redundant store.

Records in the LRDS may be updated from the Authoritative Server according to a variety of protocols, such as: based on age of records, updated whenever the records change at the Authoratative Store, or a combination of factors. The subscriber information that has been assigned to a particular LRDS will be refreshed on a periodic basis. In the event of a network outage, the PSAP will still have data available for 911 events.

In a specific embodiment, a PSAP Operator Terminal 110 will include a smart client that will interface with the Intelligent Workstation (IWS) software. The modular design will allow the same client software interface with most IWS platforms. In an alternative design, a PSAP operator terminal can access a LRDS through a standard browser.

In further specific embodiments, a system according to the invention includes a gateway specification that will guide third party providers to integrate their systems according to the invention. The gateway specification will maintain an open protocol and allow third party data providers to participate in the system.

In a further aspect, various embodiments of the present invention allow for communication with third party data providers 300 to provide additional emergency response data. A third party provider generally will be notified of an emergency event based on an in effect subscriber's agreement. In specific embodiments, a provider has the option to provide feedback which will appear in a subscriber's and/or an event log.

A third party also may be understood as a subscriber in situations where a subscriber is configured to provide real-time emergency response data. For example, a subscriber may be an industrial site that provides extensive response information during an emergency (such as plant layout or real-time sensor data) or a subscriber may be an employer with a large number of employee records that may be provided during an emergency response. In these situations, a subscriber's database may operate within a system according to the invention as a third-party database.

It will be seen that in specific embodiments of the invention as implemented in a system as shown in FIG. 3, data is distributed hierarchically, with the local source providing the first response data.

In further aspects, queries made to a local source will automatically be forwarded to up-stream servers. Queries may be forwarded to multiple upstream servers for redundancy and to improve access speed.

In specific embodiments, data in a local source includes a "Time-to-Live" option on a per server or, optionally, a per record basis. The Time-To-Live value indicates when a data record becomes outdated and needs to be refreshed from an authoritative server. The Time-To-Live value is specified on a server basis and can also be specified on a per record basis to accommodate fast changing data sources. In specific embodiments, the invention further provides a bulk query capability in the local source to allow it to bulk update records.

As indicated above, events may also be forwarded to third party data providers so they can provide feedback, e.g. an insurance company can specify that a second opinion is required or that a certain adjuster is required to inspect damage before repairs or cleanup are initiated.

A further party that may be in communication with 200 is emergency response personnel, illustrated by 310. In particular embodiments of the invention, these personnel can provide live feedback that will appear in the subscriber log.

Subscriber notification and access to data is illustrated by 400. If a subscriber has elected to receive notification regarding an event, those notifications can be sent to one or more persons to one or more notification devices, as shown in 400 via a connection 410, which in some embodiments may be an one-way connection. In a further embodiment, a subscriber can access emergency data over a two-way connection such as 420 and learn such information as whether or when response personnel were dispatched, where a victim of an event was transferred for further care, whether an insurance adjuster has been scheduled to visit the event site, etc.

According to various aspects of various specific embodiments, a system according to the invention includes architectural features to facilitate the rapid and effective provision of emergency response data. In a specific embodiment of the system shown in FIG. 3, for example, a consistent open data exchange protocol operates on connections 430. Such a consistent protocol allows for easy inclusion of third-party data during an emergency response.

Second Example System Architecture

Figure 4:
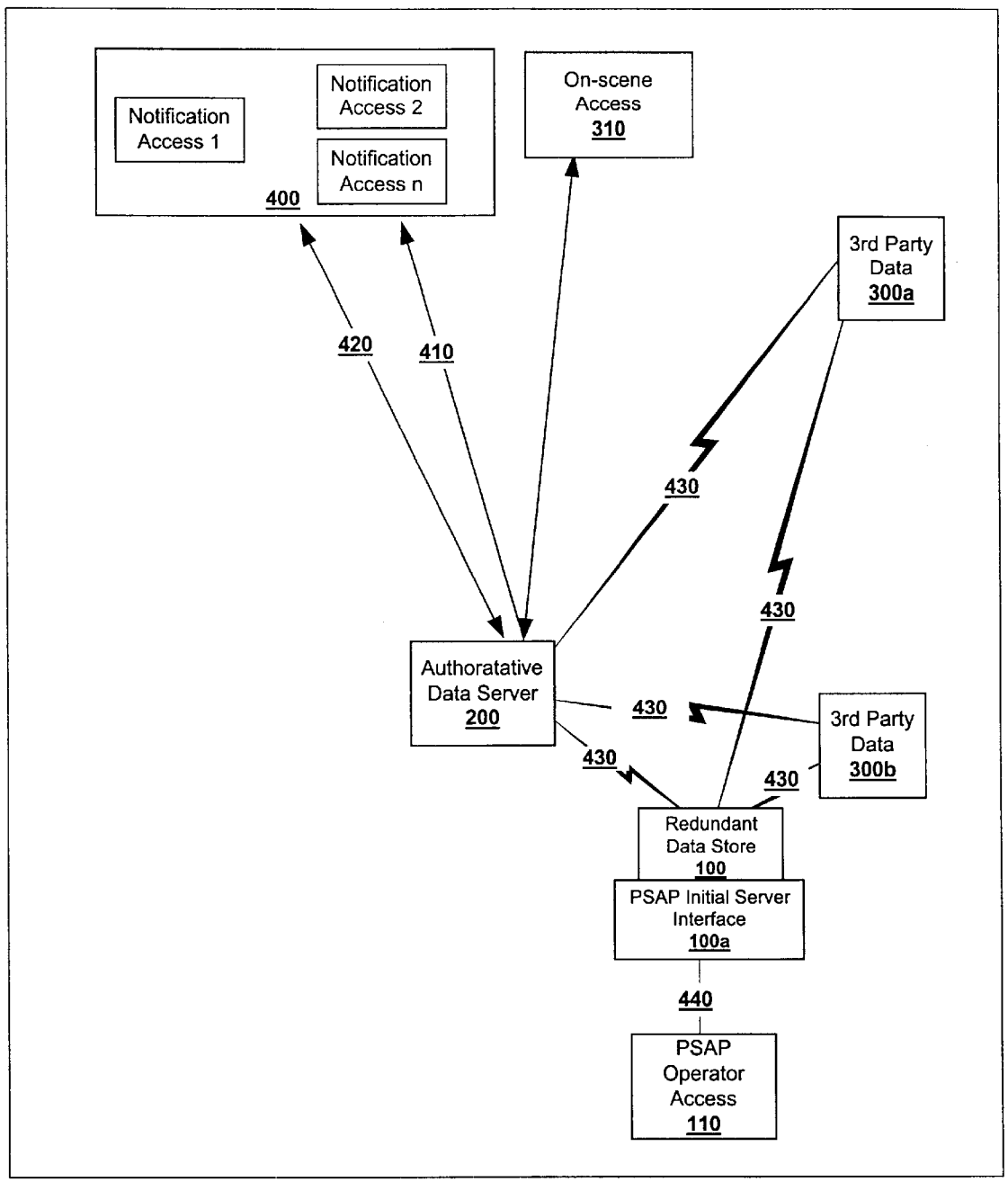
FIG. 4 is a block diagram showing an example system architecture data flow according to further specific embodiments of the invention.

FIG. 4 is a block diagram showing an example system architecture data flow according to further specific embodiments of the invention. This figure illustrates a system according to the invention as a number of functional elements. In particular embodiments, third-party data resolution and other functions necessary for interface of a PSAP terminal 110 may actually reside on the same computing device as local store 100 as a server client 100*a*. In such an embodiment, a PSAP terminal 110 can communicate over a channel 440 with a server client 100*a* and client 100*a* handles communication to a secondary data store and third-party data. In this embodiment, such an architecture allows a PSAP terminal to be an off-the-shelf type terminal or workstation without custom software, but running a standard data exchange protocol over connection 440, such as an HTTP-type protocol. Preferable, this protocol will be capable of transferring multimedia data, such as HTTP/HTML. In one embodiment, PSAP 110 could therefore connect to 100*a* with a standard WWW browser.

Data Structures

In specific embodiments of the present invention, a particular underlying data format is used to enhance the operational and architectural features. In this data format, data is self-describing, meaning that data carries in it both its field values and the respective field names and/or field characteristics of those values.

Figure 5:
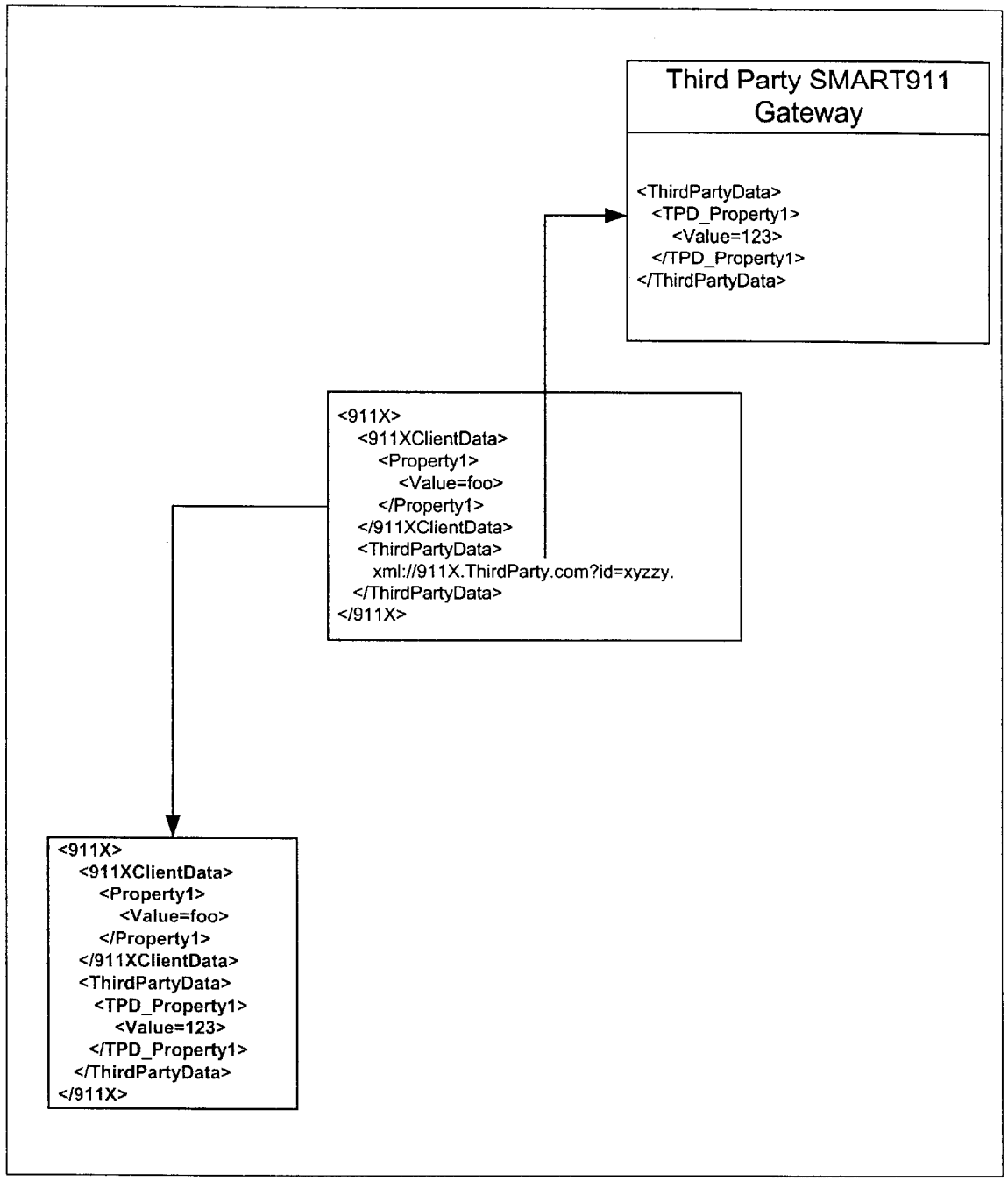
FIG. 5 illustrates an extensible and open source data architecture according to specific embodiments of the invention.

In a particular embodiment, this data structure is based on the eXtensible Markup Language (XML). A representation of an implementation based on XML is shown in FIG. 5. As indicated, in one embodiment, data at an intermediate upstream server holds a reference to the third party data. When an operator performs a query, the data reference can be resolved on-the-fly or can be delayed for on-demand lookup. The data, once retrieved, is merged into the primary data stream.

Other Features

In particular embodiments, a system or method according to the present invention can incorporate a number of additional features or aspects to enhance provision of services as herein described.

In particular embodiments, the invention can use standard HTTP in a Request/Response protocol to communicate over various of its data channels, including third-party data and log-data provided to subscribers. This allows the invention to fully utilize existing internet routing infrastructure for these channels, thereby increasing flexibility of access and reducing costs. The data exchange further may be secured using with standard security protocols such as SSL or SSH.

Embodiment in a Programmed Information Appliance

Figure 6:
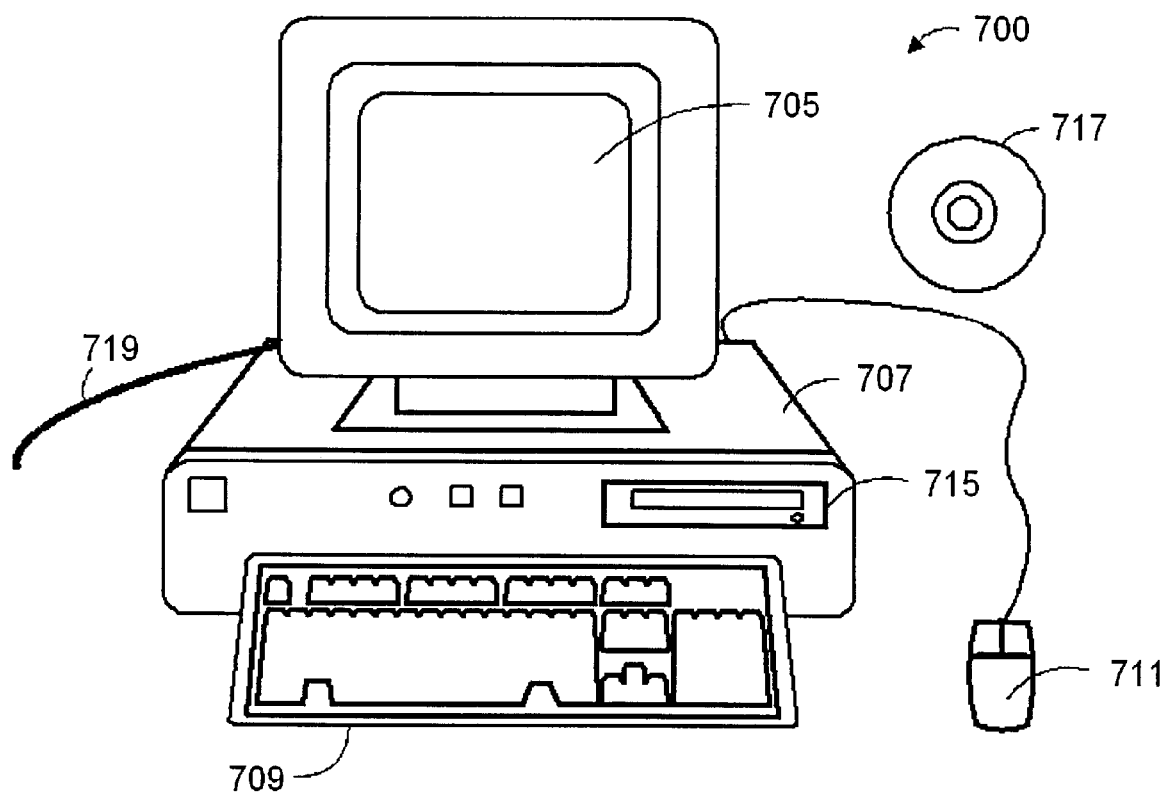
FIG. 6 is a block diagram showing a representative example logic device in which the present invention may be embodied.

FIG. 6 is a block diagram showing a representative example logic device in which the present invention may be embodied. The invention can be implemented in hardware and/or software. In some embodiments of the invention, different aspects of the invention can be implemented in either client-side logic or a server-side logic. As will be understood in the art, the invention or components thereof may be embodied in a fixed media program component containing logic instructions and/or data that when loaded into an appropriately configured computing device cause that device to perform according to the invention. As will be understood in the art, a fixed media program may be delivered to a user on a fixed media for loading in a users computer or a fixed media program can reside on a remote server that a user accesses through a communication medium in order to download a program component.

FIG. 6 shows an information appliance (or digital device) 700 that may be understood as a logical apparatus that can read instructions from media 717 and/or network port 719. Apparatus 700 can thereafter use those instructions to direct server or client logic, as understood in the art, to embody aspects of the invention. One type of logical apparatus that may embody the invention is a computer system as illustrated in 700, containing CPU 707, optional input devices 709 and 711, disk drives 715 and optional monitor 705. Fixed media 717 may be used to program such a system and may represent a disk-type optical or magnetic media, magnetic tape, solid state memory, etc. The invention may be embodied in whole or in part as software recorded on this fixed media. Communication port 719 may also be used to initially receive instructions that are used to program such a system and may represent any type of communication connection.

The invention also may be embodied in whole or in part within the circuitry of an application specific integrated circuit (ASIC) or a programmable logic device (PLD). In such a case, the invention may be embodied in a computer understandable descriptor language which may be used to create an ASIC or PLD that operates as herein described.

Other Embodiments

The invention has now been described with reference to specific embodiments. Other embodiments will be apparent to those of skill in the art. In particular, a user digital information appliance has generally been illustrated as a personal computer. However, the digital computing device is meant to be any device for interacting with a remote data application, and could include such devices as a digitally enabled television, cell phone, personal digital assistant, etc.

Also, channels have been described primarily as traditional phone lines or network connections, with the appropriate corresponding hardware. However, channels are meant to be any channels capable of carrying data, including wireless channels, optical channels, and electrical channels.

Furthermore, while the invention has in some instances been described in terms of client/server application environments, this is not intended to limit the invention to only those logic environments described as client/server. As used herein, "client" is intended to be understood broadly to comprise any logic used to access data from a remote system and "server" is intended to be understood broadly to comprise any logic used to provide data to a remote system.

It is understood that the examples and embodiments described herein are for illustrative purposes only and that various modifications or changes in light thereof will be suggested by the teachings herein to persons skilled in the art and are to be included within the spirit and purview of this application and scope of the claims.

CONCLUSION

The invention has now been explained with regard to specific embodiments. Variations on these embodiments and other embodiments may be apparent to those of skill in the art. The invention therefore should not be limited except as provided in the attached claims. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed:

1. A method of providing emergency response information comprising:
   receiving a request for emergency response data;
   retrieving emergency response data from initial storage;
   initiating one or more requests for third-party data;
   using an open protocol data structure; and
   presenting available emergency response data to a user.

2. A method according to claim 1 further comprising:
   merging responses to said one or more requests for third-party data into data presented to a user.

3. A method according to claim 1 wherein said presenting includes indications that requested third-party data is yet to be received.

4. A method according to claim 1 wherein said third-party data is maintained by at least one third-party data manager using one or more data formats different from a format used for said initial storage.

5. A method according to claim 4 wherein a portion of said third-party data is resident on at least one third-party computer system including a resident agent for formatting responses to said requests for third-party data.

6. The method according to claim 1 further comprising:
during an emergency event initiating a contact to an authorized recipient.

7. The method according to claim 1 further comprising:
maintaining an event log for an emergency response event.

8. The method according to claim 7 further comprising:
allowing a third-party to write data to said event log.

9. The method according to claim 7 wherein said event log may include a schedule of follow-up tasks some of which may be supplied by said third-party data sources.

10. The method according to claim 7 wherein said event log is accessible to an authorized user over a public access data network during an emergency.

11. A method of providing emergency response information using an open protocol data structure comprising:
initiating a request for emergency response data at a PSAP;
attempting to respond to said request at an initial data source;
at said initial data source, forwarding said request to one or more upstream authoritative servers;
retrieving a data record and initiating requests for external data;
at an upstream authoritative server, formatting and merging external data for transfer to said local data source.

12. A method according to claim 11 wherein said external requests are transmitted using a standard transfer protocol.

13. A method according to claim 12 wherein said requests are transmitted using HTTP.

14. A method according to claim 11 wherein responses to said requests for external data are encoded in a self-describing data format.

15. A method according to claim 14 wherein responses to said requests for external data are encoded in an XML compatible data format.

16. A method according to claim 14 wherein data fields in a record can reference other data sources.

17. A method for representing and processing emergency response data in an emergency response server comprising:
receiving a request for subscriber emergency response data:
retrieving a record for said subscriber, said record including one or more references to third party data;
attempting to resolve said one or more references by initiating requests for third-party data; and
merging received third-party data with said record to compose a response to said request for subscriber emergency response data and presenting said merged response to a requester.

18. A method according to claim 17 wherein said merged response can include data retrieved from a third-party or can include an indication that additional data may be available regarding said record.

19. An emergency response data storage hub system comprising:
an interface for communicating with one or more PSAP systems;
an interface for communicating with one or more third-party data providers;
an interface for communicating with an on-scene emergency response provider;
an interface for communicating with one or more subscriber specified endpoints;
a data resolution and merge process able to:
read stored data records with embedded external data references;
initiate requests for external data; and
merge external data into a record for deliver to a PSAP.

20. A system according to claim 19 further comprising:
an interface for communicating with one or more local redundant data stores; and
logic routines allowing for the bulk updating of data on said one or more local redundant data stores.

21. A system according to claim 19 further comprising:
emergency response log storage able to store ongoing emergency response data and activities for access by authorized users.

22. A system according to claim 21 further comprising:
an interface allowing automatic access to an emergency response log by an authorized user.

* * * * *